United States Patent [19]
Wilcox et al.

[11] Patent Number: 5,995,077
[45] Date of Patent: *Nov. 30, 1999

[54] PORTABLE, WEARABLE READ/WRITE DATA DEVICE

[75] Inventors: Walter W. Wilcox, Julian; Michael R. Galarneau, San Diego, both of Calif.; Clark E. Fortney, Gahanna; Richard D. Rosen, Hilliard, both of Ohio

[73] Assignee: The United States of America as represented by the Secretary of the Navy, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/594,481

[22] Filed: Jan. 31, 1996

Related U.S. Application Data

[63] Continuation of application No. 08/277,802, Jul. 20, 1994, abandoned.

[51] Int. Cl.[6] .................................................. G09G 5/00
[52] U.S. Cl. ........................ 345/112; 345/507; 40/447; 369/41; 128/920; 235/379
[58] Field of Search .................. 365/900; 369/77.1, 369/83; 235/379, 380, 382.5; 128/630, 920; 962/26, 4, 5; 40/625–633, 447–452; 345/112, 185, 203, 507; 368/41

[56] References Cited

U.S. PATENT DOCUMENTS

| | | | |
|---|---|---|---|
| 4,211,919 | 7/1980 | Ugon | 235/487 |
| 4,298,793 | 11/1981 | Melis et al. | 235/487 |
| 4,348,740 | 9/1982 | White | 364/410 |
| 4,348,744 | 9/1982 | White | 364/410 |
| 4,385,291 | 5/1983 | Pignet | 368/41 |
| 4,591,974 | 5/1986 | Dornbush et al. | 364/222.2 |
| 4,650,981 | 3/1987 | Foletta | 235/449 |
| 4,724,310 | 2/1988 | Shimamura et al. | 902/26 X |
| 4,829,166 | 5/1989 | Froelich | 235/379 |
| 4,839,806 | 6/1989 | Goldfischer et al. | 364/479.01 |
| 4,852,570 | 8/1989 | Levine | 128/906 |
| 4,868,376 | 9/1989 | Lessin et al. | 235/492 |
| 4,895,161 | 1/1990 | Cudahy et al. | 128/630 X |
| 4,975,842 | 12/1990 | Darrow et al. | 128/923 |
| 5,012,229 | 4/1991 | Lennon et al. | 345/507 |
| 5,025,374 | 6/1991 | Roizen et al. | 128/920 |
| 5,061,845 | 10/1991 | Pinnavaia | 235/492 |
| 5,239,166 | 8/1993 | Graves | 902/26 X |
| 5,247,164 | 9/1993 | Takahashi | 235/492 |
| 5,379,401 | 1/1995 | Robinson et al. | 235/492 X |

OTHER PUBLICATIONS

NHRC Report No. 93–21 Nov. 1993.

NHRC Report No. 93–31 May 1993.

Abstract of presentation made at American Medical Informatics Association, Sep. 1994 Spring Congress.

Copy of article appearing in May/Jun. 1994 issue of Navy Medicine Naval Medical Research and Development Command Highlights p. 34.

*Primary Examiner*—Amare Mengistu
*Attorney, Agent, or Firm*—A. David Spevack

[57] ABSTRACT

A wearable electronic data collection and storage device is used for recording field medical data. The device is small, portable and easily worn, similar to a watch or medallion and is capable of interfacing with a large, external accessing system. The device includes an application specific integrated circuit card which is received in and is removable from a wearable/portable data entry, storage and retrieval device. The card includes a programmable memory for storing data. These two elements, when combined, form the MEDTAG unit. This unit also includes a memory for storing software, and a microprocessor for reading and entering data, and executing the software. The wearable/portable data entry storage and retrieval device includes an electrical connection to the removable card, a display for showing menus and data to a user, and two manual input buttons allowing the user to select from the menus and enter data into the programmable memory of the card.

8 Claims, 5 Drawing Sheets

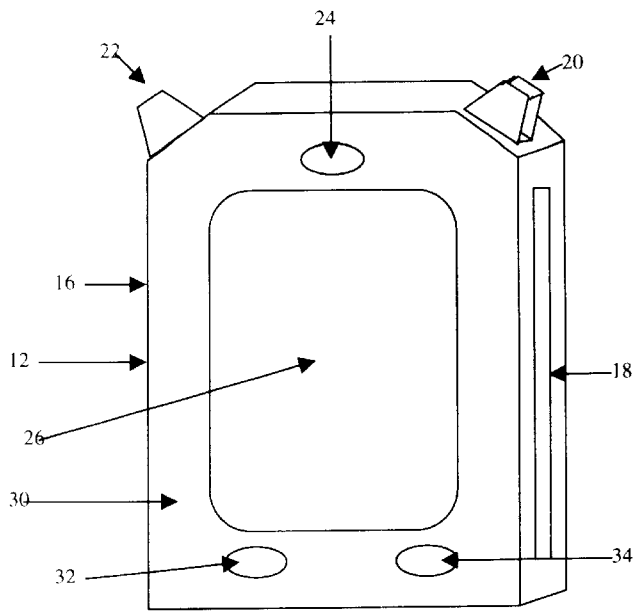
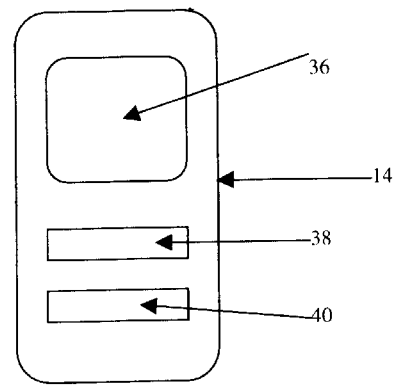
FIG 1A  FIG 1B
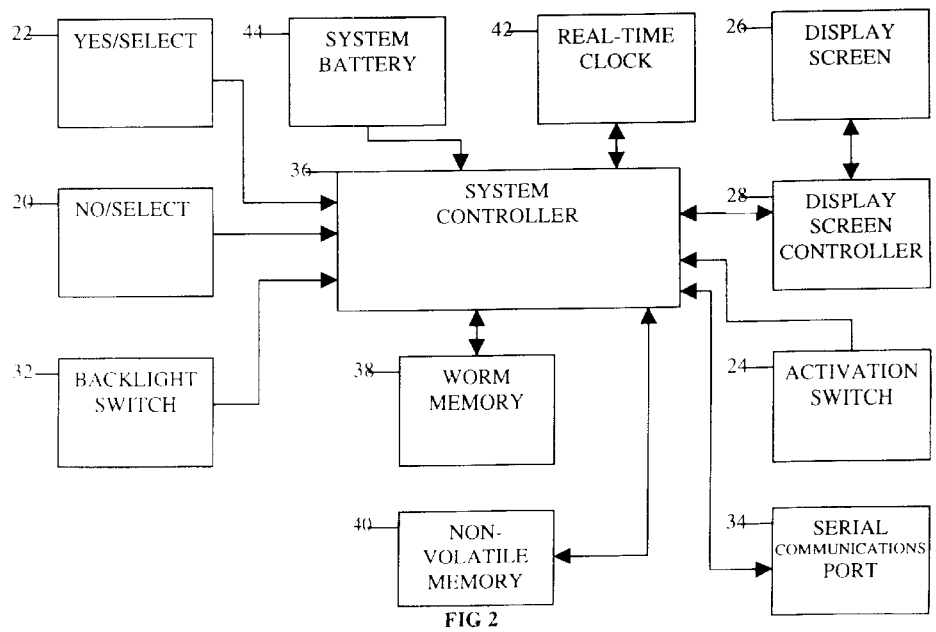
FIG 2

PORTABLE, WEARABLE READ/WRITE DATA DEVICE

This is a Continuation of copending application 08/277,802, filed 20 Jul. 1994, now abandonded.

BACKGROUND OF THE INVENTION

1. Field of the Invention

The present invention relates to an electronic data storage device which is small, portable, easily worn, and capable of interfacing with an external accessing system.

2. Description of the Prior Art

Currently, in order to obtain battlefield medical data, a field medical card (DD Form 1380) is used. The field medical card is carried in a booklet by corpsmen and medics along with some type of writing implement. Once treatment has been performed, the field medical card is used to record patient identification information and pertinent medical data. Once completed, the form must be attached to the patient.

A number of obvious problems exist with this current method. For example, the form takes too long to complete, it is difficult to perform documentation at night, handwriting is often illegible, and writing instruments are highly susceptible to being lost or broken. In addition, the form is often subjected to intense environmental abuse which can obliterate that documentation which has been completed. As a result, combat casualty information recorded with the current system is generally inaccurate and incomplete.

Considering some of the patented art in this field, U.S. Pat. No. 5,012,229 to LENNON et al. discloses a wearable personal/medical information device which includes a data display. Items of personal and/or medical information are stored in the device. Switches are used to display different storage data.

The device includes a detachably mounted read-only memory (ROM) unit for storing personal or medical information which is not subject to change as well as preset display data. The information stored on the ROMs of this unit may only be altered at a remote facility. Items of information which a wearer may want to change periodically are loaded in an internal RAM which may be laboriously altered using a push button to select characters one at a time, or requires a jack and a hand-held keyboard.

U.S. Pat. No. 5,025,374 to ROIZEN et al. discloses an interactive medical test selector for use by a patient having a screen for displaying questions to the patient, a limited number of keys by which the patient can enter answers, and a memory device for storing the patient's answers. A portion of the device is easily removable for updating the questions or altering the language of the questions. This removable portion consists of a ROM providing the operating program in the text for the device, but does not store data. The ROM does not include any individualized information about the patient.

More generally, U.S. Pat. No. 4,591,974 to DORNBUSH et al. discloses a system for recording data about a patient under treatment using a hand-held computer and transferring that data to a host computer. The hand-held computer is merely used to update information on the host computer and does not itself contain a complete patient history. Further, the few details provided about the hand-held computer indicate that it has no easily removable parts and only uses conventional data entry.

SUMMARY OF THE INVENTION

It is an object of the present invention to overcome problems inherent in the current manual method of documenting battlefield casualty medical data while also providing important advantages over the patented art.

The present invention achieves this objective through the provision of an application specific integrated circuit card in conjunction with a wearable data entry, storage and retrieval device. The data entry storage and retrieval device includes a housing for removably receiving the card therein to form the unit. The card includes a programmable memory for storing data. The unit also includes a memory for storing software and a microprocessor for reading and entering data and executing the software data. The device further comprises means for providing an electrical connection to the card, means for displaying menus from the software and data to a user, and manual input means allowing the user to select from the menus and enter data into the programmable memory of the card.

Other objects, features, and advantages of the invention will be set forth or be apparent from the following description of the preferred embodiments of the invention.

BRIEF DESCRIPTION OF THE DRAWINGS

FIG. 1a is a front view of a wearable data entry, storage and retrieval device in accordance with a preferred embodiment of the present invention;

FIG. 1b is a front view of an application specific integrated circuit card (ASICC) according to a preferred embodiment of the present invention; and FIG. 2 is a block diagram of the entire unit in accordance with a preferred embodiment of the present invention.

DETAILED DESCRIPTION OF THE INVENTION

Figure 3A:
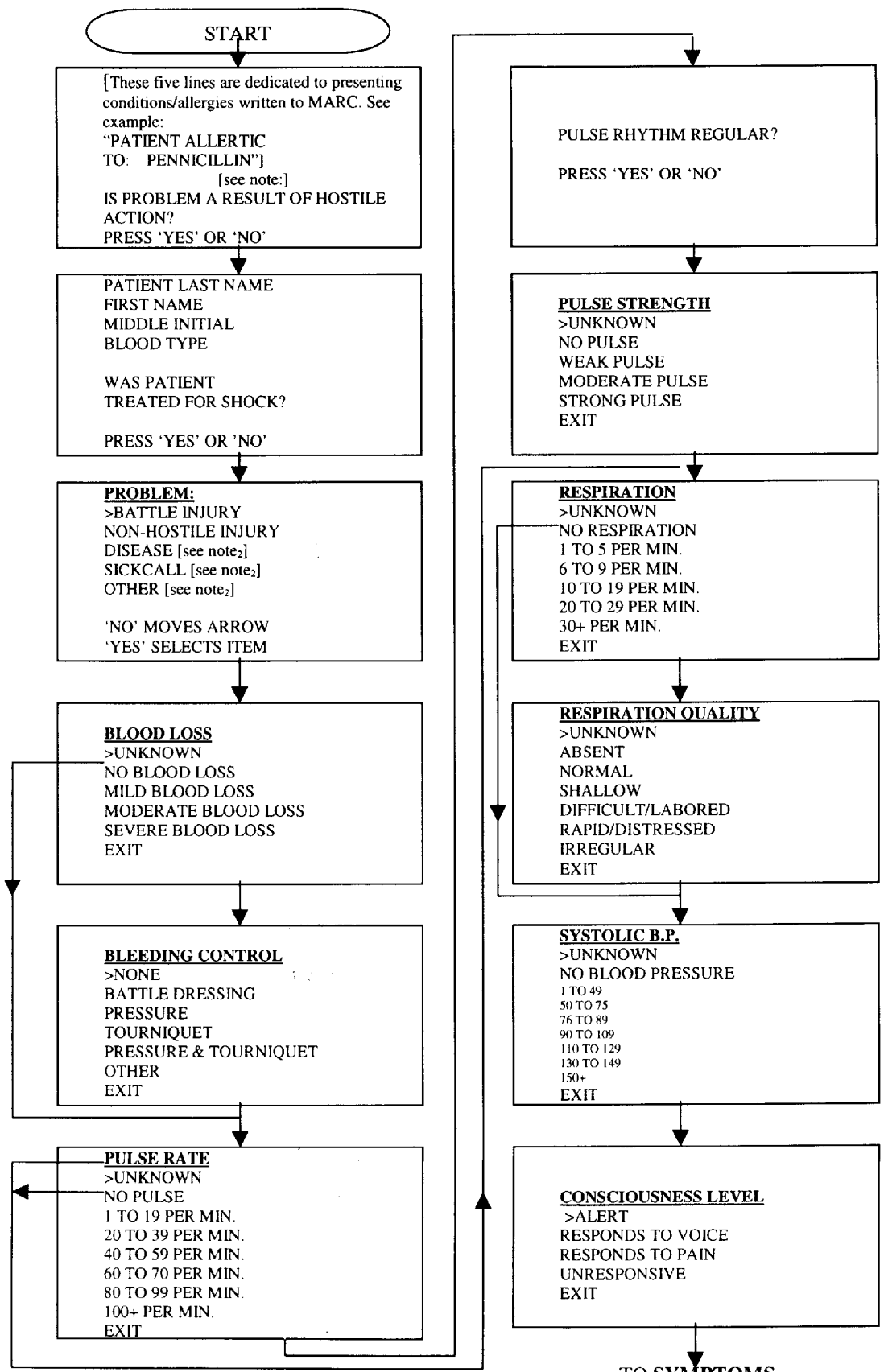
FIGS. 3a, 3b, 3c, and 3d are flow chart examples of the software menus and data items.

Referring to FIG. 1a, there is shown a data entry, storage, and retrieval device constructed in accordance with a preferred embodiment of the invention. The device includes a housing 100 and the data entry, storage, and retrieval controls. Specifically, at the top of housing 100, at the corners thereof, are two control buttons 110, 120 for entry and retrieval of field medical data. An activation switch 130 located at the center of the top of housing 100 places the device in the data capture/retrieval mode of operation.

A screen 140 provided on the front face of housing 100 is used to display menus, to provide the user with information collecting capability, as well as to display personal identification, pre-existing medical conditions, and a portable data card portion at 150.

An illumination switch 160 located below display 140 provides backlight illumination for display 140, while a serial port 170, also located below display 140, allows the device to be connected to a personal computer or some other reader/writer device. A slot 180 in the side of housing 100 accepts a portable data carrier element of the device which is described below.

The data entry, storage, and retrieval device contains internal electronics which do not have any individualized information stored therein. Since this data entry, storage and retrieval device is not individualized, a failed device may readily be replaced by another such device, thus permitting a convenient redundancy.

FIG. 1b shows a preferred embodiment of the portable data carrier element of the present invention. The portable data carrier, which is generally denoted 115 in FIG. 1b, includes, in this embodiment, electronic content and associated computer chips comprising a microprocessor chip 125, a read only program memory 135, and a non-volatile memory, such as electronically erasable programmable ROM (EEPROM) 145. Personal identification information, such as name, rank, social security number, sex, nation, force, unit, specialty, religion, allergies, blood type, etc., are pre-loaded into the non-volatile memory 145 from a personal computer via the serial communications port 170 of the data entry, storage and retrieval device.

Prior to deployment to the theater, military personnel wear only the data carrier portion of the device. The data carrier 115 remains inactive and functions solely as a personal identification tag much in the same way as the currently used "dog tag" functions, including having human readable information provided thereon.

Upon deployment to the theater of operations, the data carrier 115 is mated, by the insertion thereof into slot 180 of housing 100, with the data entry, storage, and retrieval device. The make-up of the electrical system overall unit, i.e., with card 115 received in slot 180, is shown in the block diagram of FIG. 2.

Initially, the unit of FIG. 2 will be in a resting mode with all of the components being off except for the real time clock 215. Pressing the "yes" or "enter" switch 110 will display system status information, such as battery condition and personnel identification, on display screen 140 for as long as switch 110 is activated.

In one embodiment, an injured individual's unit can be activated by corpsman, buddy or the casualty himself. A deliberate action will be required in order to avoid accidental activation. This activation is provided by activation switch 130. Once activated, the unit cannot be deactivated by anything other than an external privileged reader/writer (not shown). In another embodiment, the two elements of the unit would be carried separately until an injury occurs. Upon injury, the unit could then be activated by inserting the portable data card into the device. The unit is deactivated when the card is removed.

Figure 3B:
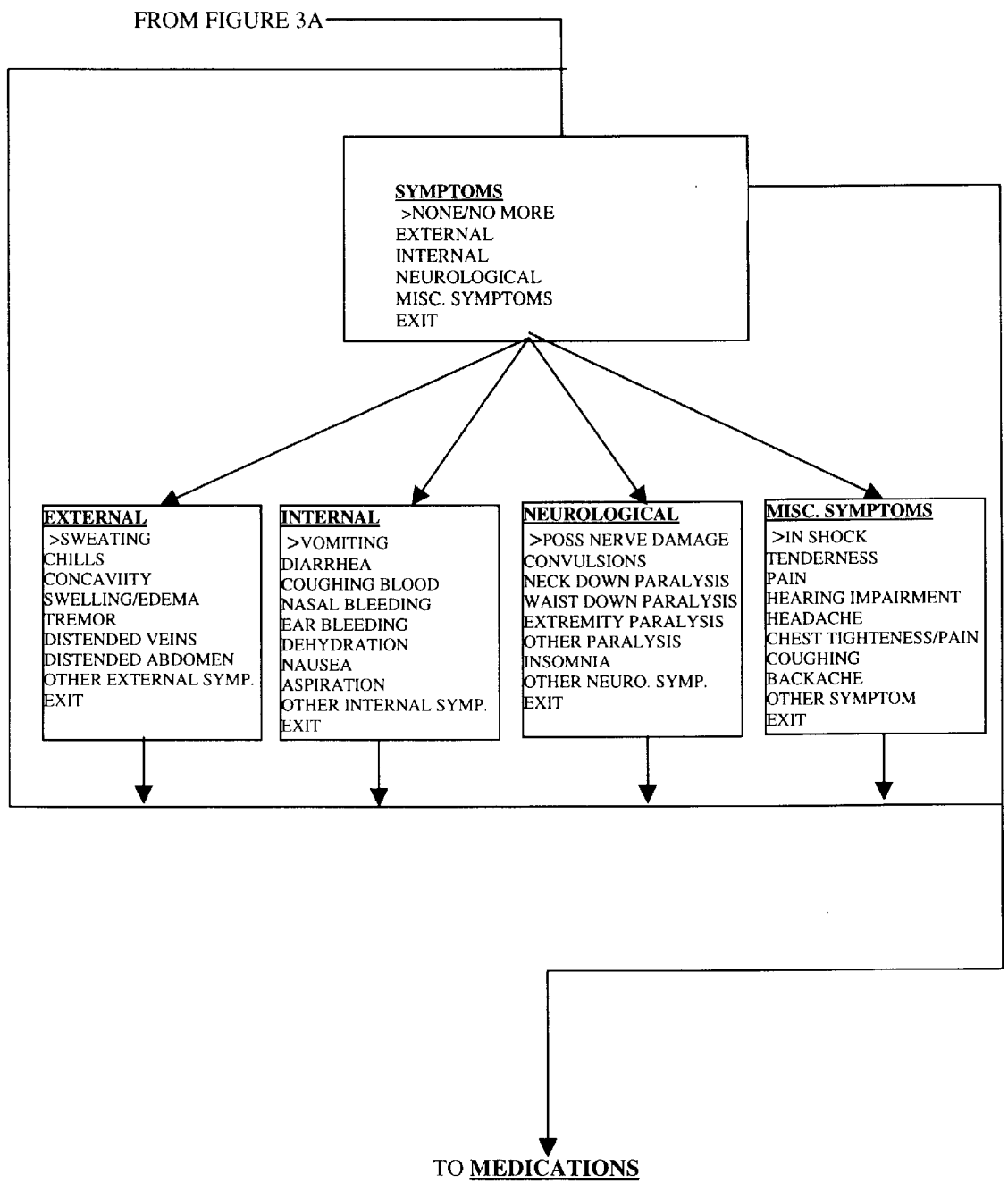
Figure 3C:
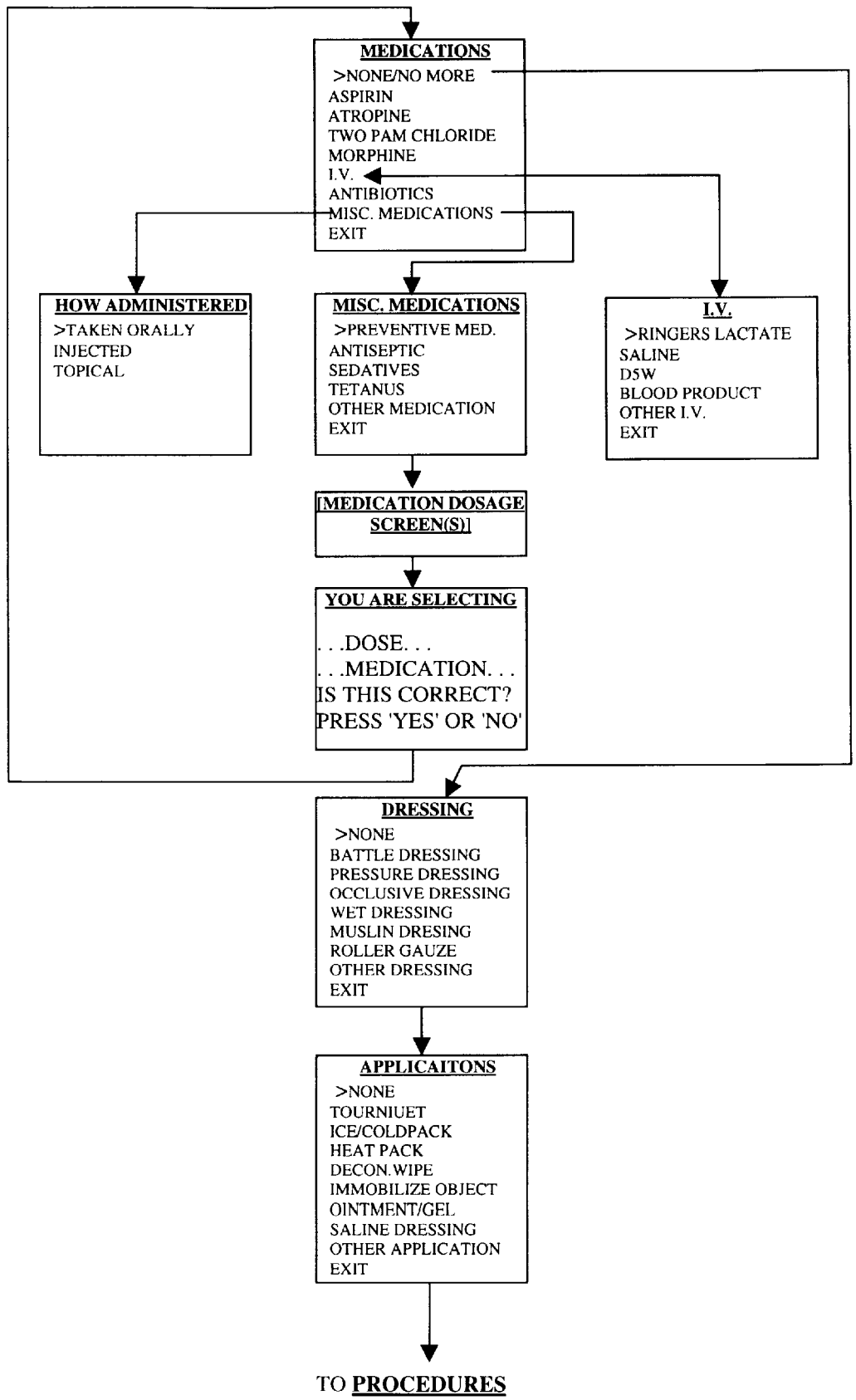
Figure 3D:
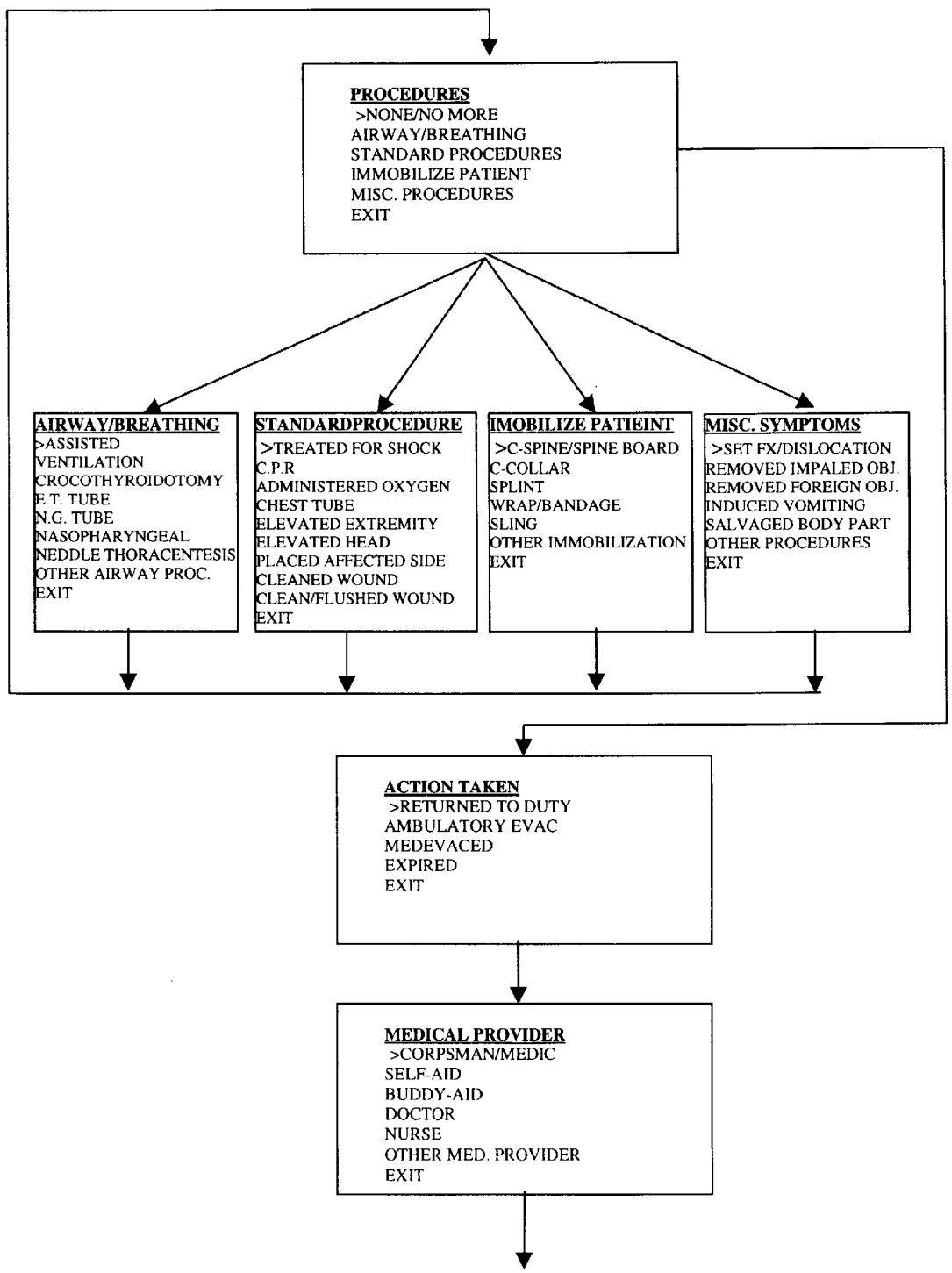

When the unit is activated, it enters the data capture/retrieval mode of operation, and screen 140 displays data entry menus. The data elements in the menus provide the user with the ability to both record and retrieve patient information related to injury/problem assessment, treatments administered, patient condition and patient disposition (see FIGS. 3a, 3b, 3c, and 3d). Reassessment of patient condition, as well as other updated information, may also be recorded at some future time.

It is to be understood that only the two buttons 110 and 120 are required to enter and retrieve the information. The "yes" or "enter" switch 110, when the unit is activated, is used to enter data selections using the menu system. The "no" or "select" switch 120 is used to move an indicator around on the display screen 140 in order to choose from a menu of data selections.

The read only program memory 135 contains the software used for running the unit. Microprocessor 125 is used to execute the software and control reading and storage of the data items. The -non-volatile memory 145 stores both the pre-loaded and the entered data items, is non-volatile and will maintain its contents without power. The unit will enter a standby mode after a predetermined period, e.g., ten minutes, of inactivity. When the "yes" switch 110 is pressed, the device reverts back to data/capture retrieval mode discussed above.

FIG. 3 shows exemplary data item categories which may be stored in the memory of the unit. These exemplary items parallel the items contained on the current field medical card (DD Form 1380) and are displayed to the user by means of standard programming protocols. The date and time of injury will be recorded automatically when the unit is activated. Identification information will remain constant in the unit at all times after initialization. The remaining items may be entered through menu selections.

In a preferred embodiment, power to the unit is supplied internally by means of a watch type battery that provides power to the system controller 125, non-volatile memory 145, read only program memory 135, the display screen 140 with backlight and serial port 170. Power control circuit or module 210 supplies power to these components whenever either the activate or "yes" switch 130 is closed. The battery 210 supplies power to these components whenever the system controller activates a display on/off signal for display screen 140.

The real time clock circuit or module 215 keeps track of the time and date at all times. Patient identification and field treatment history can be transferred to other medical record-keeping systems via serial port 170 or may be transferred via the portable data card by means of an external card read/write device (not shown). The transfer mode may be selected from the menu displayed in the data capture/retrieval mode. After the data has been transferred, the unit will revert back to the data capture/retrieval mode, unless deactivation has been initiated.

In an important alternative embodiment of the invention, all of the generic electronic elements, (e.g. microprocessor 125 and read only memory 135) are located in the data entry, storage and retrieval unit, and only the non-volatile memory 145, containing the individualized information is located on the portable data card. This may help simplify the construction and minimize the size of the card.

The embodiments discussed above are clearly only illustrative. For example, many different menus may be used in conjunction with the present invention. Further, the placement of the "yes" and "no" buttons 110 and 120, while illustrated in this embodiment as being located in typical positions for a stopwatch, may be placed in different positions, e.g., both on the top of the device or both on the side of the device, parallel to each other. Further, many different devices, such as a metal guard around the activation switch 130, may be employed in order to avoid accidental activation of the unit. Also, the internal adjustment for the backlighting intensity may be made external.

Although the present invention has been described above relative to exemplary preferred embodiments thereof, it will be understood by those skilled in the art that variations and modifications can be effected in these embodiments without departing from the scope and the spirit of the invention as defined in the claims which follow.

What is claimed is:

1. A method of data capture/retrieval on the scene of field gathered medical data by using a portable, wearable, hand-holdable electronic data storage device having a portable, wearable, hand holdable, read/write data entry, storage and retrieval portion and a card portion comprising the steps of:
    inserting said card portion of said electronic data storage device into a slot of said read/write device portion thereof so as to form said electronic data storage device and activate a data capture/retrieval mode of operation thereof;
    storing personal identification data in a non-volatile memory of said card portion of said electronic data storage device;

displaying sequentially a tree of medical data entry menus on a display screen of said read/write device portion;

navigating through said tree of data entry menus and selecting data from said tree of data entry menus by depressing a yes/select or no/don't select switch as the sole means for controlling passage through the tree of data entry menus, said yes/select and no/don't select switches mounted on said read/write device portion;

entering data selected from said tree of data entry menus by depressing a yes/select switch mounted on said read/write portion to create field entered data; and storing said field entered data into said non-volatile memory of said card portion of said system.

2. The method of claim 1 comprising the additional steps of:

storing in said non-volatile memory the date/time when said field entered data is created; and displaying on said display screen, said personal identification data and said entered data from said non-volatile memory.

3. The method of claim 2 comprising the additional steps of:

transferring to said read/write device portion said personal identification data.

4. A portable, wearable, hand holdable, electronic read/write data storage system for selecting and entering, field gathered medical data on the scene of a medical incident by a user consisting of:

a portable, wearable, hand holdable, read/write data entry, storage and retrieval portion including a housing, said housing being configured to have at least a front face portion, and side portions, a display screen controller including a display screen said display screen in the front portion and a slot configured in a side portion of said housing, a no/don't select switch and a yes/select switch on said housing as the sole means for controlling navigation through a tree of medical data menus displayed on said screen and for selecting specific menu items displayed on said screen by said user, said yes/select switch disposed on said housing at a position separated from said no/don't select switch for entering of the selected menu items as field generated medical data by said user; and a card portion configured to be inserted into and be removable from said slot of said housing to provide an electrical connection to said card portion when insert, thereby forming said electronic read/write data storage system; said system further comprising;

a first non-volatile memory having stored therein said tree of medical data menus;

a system controller including a microprocessor for executing a software program to display said tree of medical data menus on said screen, and scan, read only, select and write from said tree of menus in said first non-volatile memory;

a second nonvolatile memory operatively connected to the system controller to read/write and store field gathered and selected medical data from said tree of medical data menus on said first non-volatile memory.

5. The portable, wearable, hand holdable, electronic read/write data storage system of claim 4, wherein the system controller and the first non-volatile memory containing the tree of menus are in the read/write portion of the system and the second non-volatile memory recording the field gathered medical data is in the card portion of said system.

6. The portable, wearable, hand hold able, electronic read/write data storage system of claim 5 wherein said system further comprises;

a backlight switch disposed on said read/write portion and being operatively connected to the display screen for backlight illumination thereof;

a serial communications port disposed on said read/write portion to allow said portable, device portion to be operatively connected to a computer for data transfer;

information pre-loaded and programmable in an electronically erasable programmable read-only memory module.

7. The portable, wearable read/write data storage system of claim 6 wherein said card portion further comprises:

a read/write once read many memory operatively connected to said system controller when inserted in said read/write device portion and having stored therein personal identification data and medical data; and a non-volatile memory operatively connected to said system controller and having stored therein said field gathered and entered medical data items.

8. The electronic portable, wearable, handholdable, read/write data storage system of claim 7 wherein said read/write device portion further comprises:

a real-time clock operatively connected to said non-volatile memory via said system controller for recording the date/time at which said user enters, via said yes/select switch, said selected field gathered data items of the medical data; and a system battery operatively connected to said system controller, said read-only memory, said non-volatile memory, said read-only memory, said display screen and said serial communications port for supplying power thereto whenever either said activation switch or said yes/select switch is depressed.

* * * * *